United States Patent [19]

Isawa et al.

[11] Patent Number: 5,624,948
[45] Date of Patent: Apr. 29, 1997

[54] 1-(2-BENZIMIDAZOLYL)-1,5-DIAZACYCLOOCTANE COMPOUNDS

[75] Inventors: Hidetoshi Isawa; Nobuko Yanagi; Yasuo Takehana, all of Nagano; Den-ichi Momose; Masaaki Satoh, both of Matsumoto; Yoshinori Nonaka, Nagano, all of Japan

[73] Assignee: Kissei Pharmaceutical Co., Ltd., Japan

[21] Appl. No.: 537,747

[22] PCT Filed: May 16, 1994

[86] PCT No.: PCT/JP94/00787

§ 371 Date: Nov. 14, 1995

§ 102(e) Date: Nov. 14, 1995

[87] PCT Pub. No.: WO94/27973

PCT Pub. Date: Dec. 8, 1994

[30] Foreign Application Priority Data

May 20, 1993 [JP] Japan ................ 5-155995

[51] Int. Cl.$^6$ ................ A61K 31/415; C07D 403/04
[52] U.S. Cl. ................ 514/395; 514/183; 540/470
[58] Field of Search ................ 540/470; 514/183, 514/395

[56] References Cited

U.S. PATENT DOCUMENTS

| | | | |
|---|---|---|---|
| 4,835,161 | 5/1989 | Janssens et al. | 514/303 |
| 4,943,580 | 7/1990 | Janssens et al. | 514/303 |
| 4,988,689 | 1/1991 | Janssens et al. | 514/212 |
| 5,461,059 | 10/1995 | Bonnet et al. | 514/265 |

FOREIGN PATENT DOCUMENTS

| | | | |
|---|---|---|---|
| 0005318 | 3/1979 | European Pat. Off. | C07D 471/04 |
| 0079545 | 11/1982 | European Pat. Off. | C07D 235/30 |
| 0151824 | 12/1984 | European Pat. Off. | C07D 471/04 |
| 0232937 | 1/1987 | European Pat. Off. | C07D 471/04 |

Primary Examiner—Philip I. Datlow
Attorney, Agent, or Firm—Depaoli & Frenkel, P.C.

[57] ABSTRACT 1-(2-benzimidazolyl)-1,5-diazacyclooctane compounds represented by the formula:

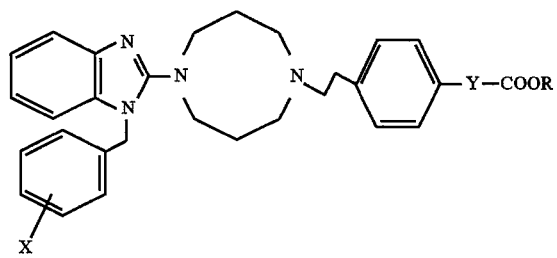

wherein X represents a hydrogen atom or a halogen atom; Y represents a covalent bond, a straight- or branched-chain alkylene group having 1 to 6 carbon atoms, or a straight- or branched-chain alkenylene group having 2 to 6 carbon atoms; R represents a hydrogen atom, or a straight- or branched-chain alkyl group having 1 to 6 carbon atoms; and pharmaceutically acceptable salts thereof. The compounds represented above are novel potent and long-lasting histamine HI-receptor antagonist with less-topical irritation, and can be topically administered by inhalation for the treatment of bronchial asthma.

9 Claims, No Drawings

1

1-(2-BENZIMIDAZOLYL)-1,5-DIAZACYCLOOCTANE COMPOUNDS

This is a National Stage Application under 35USC371 of International Application PCT/JP94/00787 filed May 16, 1994.

TECHNICAL FIELD

The present invention relates to novel 1-(2-benzimidazolyl)-1,5-diazacyclooctane compounds and pharmaceutically acceptable salts thereof being useful as therapeutic agents.

More particularly, the present invention relates to novel 1-(2-benzimidazolyl)-1,5-diazacyclooctane compounds represented by the formula:

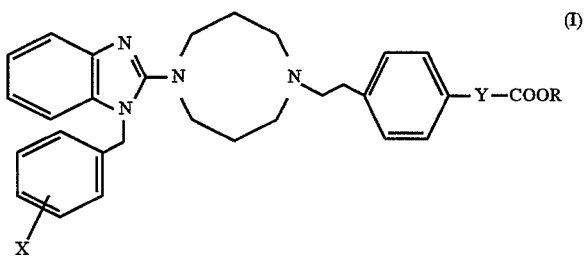

(I)

wherein X represents a hydrogen atom or a halogen atom; Y represents a covalent bond, a straight- or branched-chain alkylene group having 1 to 6 carbon atoms, or a straight- or branched-chain alkenylene group having 2 to 6 carbon atoms; R represents a hydrogen atom, or a straight- or branched-chain alkyl group having 1 to 6 carbon atoms; and pharmaceutically acceptable salts thereof.

BACKGROUND ART

Histamine $H_1$-receptor antagonists are widely employed in orally for the treatment of bronchial asthma, and it is reported that they often show systemic adverse actions such as sedation or arrhythmogenetic activity. Therefore, topical treatment using the antagonists has been attempted in order to avoid such adverse actions. However, the methods are unsuccessful because the antagonists have strong bronchia irritation when inhaled directly to the bronchia.

Thus, there remains a need for the development of histamine $H_1$-receptor antagonists which can be directly inhaled to the bronchia for the treatment of bronchial asthma with less irritation to bronchial tissues.

European Patent Application Unexamined Publication No. 5,318 discloses a benzimidazole compound represented by the formula:

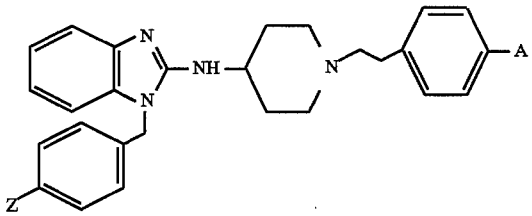

wherein Z represents a hydrogen atom or a fluorine atom; A represents a methoxy group, an ethoxy group, a 2-propenyloxy group, a hydroxy group, a methoxycarbonylmethyloxy group, an methoxycarbonylmethyloxy group, a cyanomethyloxy group, a methylthio group, a methanesulfonyl group, an amino group, a nitro group, a fluorine atom or a chlorine atom. In addition, of the above benzimidazole compounds, the compound represented by the formula:

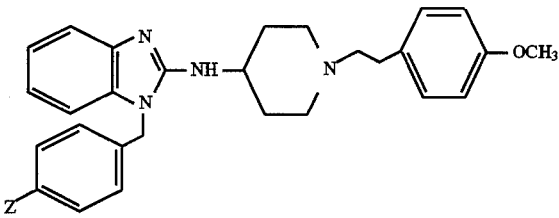

has been employed (general name: Astemizole) as oral histamine $H_1$-receptor antagonist. However, any topical formulation of this drug applied to the bronchia has not been acceptable in practice due to strong irritation to bronchial tissues.

The 1-(2-benzimidazolyl)-1,5-diazacyclooctane compounds of the present invention are novel compounds, and have not been disclosed or suggested in any prior literature.

DISCLOSURE OF THE INVENTION

The object of the present invention is to provide novel 1-(2-benzimidazolyl)-1,5-diazacyclooctane compounds and pharmaceutically acceptable salts thereof which are useful as therapeutic agents for the treatment of bronchial asthma by inhalation to the bronchia.

Another object of the present invention is to provide pharmaceutical composition containing a 1-(2-benzimidazolyl)-1,5-diazacyclooctane compound or a pharmaceutically acceptable salt thereof as an active ingredient, which is effective for the treatment of bronchial asthma by inhalation to the bronchia.

A further object of the present invention is to provide the use of a 1-(2-benzimidazolyl)-1,5-diazacyclooctance compound or a pharmaceutically acceptable salt thereof for the manufacture of a pharmaceutical for the treatment of bronchial asthma.

Still further object of the present invention is to provide a method for the treatment of bronchial asthma, which comprises inhaling to the bronchia a therapeutically effective amount of a 1-(2-benzimidazolyl)-1,5-diazacyclooctane compound or a pharmaceutically acceptable salt thereof.

Other objects, feature and advantages of the present invention will become apparent from the following description of the invention.

The present invention provides novel 1-(2-benzimidazolyl)-1,5-diazacyclooctane compounds and pharmaceutically acceptable salts thereof which exhibit potent antihistaminic and antiallergic activities with less topical irritations, and particularly irritation to bronchial tissues. Thus, the 1-(2-benzimidazolyl)-1,5-diazacyclooctane compounds of the present invention can be useful as therapeutic agents for the treatment of bronchial asthma by inhalation to the bronchia.

In the definition of the compounds represented by the formula (I), the term "alkylene group" as used herein means a straight- or branched-chain alkylene group having 1 to 6 carbon atoms such as a methylene group, an ethylene group, a trimethylene group, a tetramethylene group, a pentamethylene group, a hexamethylene group, a 1,1-dimethylethylene group, a propylene group, an ethylethylene group, a 1-methyltrimethylene group, a 1,1-dimethyltrimethylene group, a 2-methyltrimethylene group, a 2,2-dimethyltrimethylene group, and the like.

The term "alkenylene group" as used herein means a straight- or branched-chain alkenylene group having 2 to 6 carbon atoms such as a vinylene group, a propenylene group, an isopropenylene group, a 1-butenylene group, a 2-butenylene group, and the like.

The term "alkyl group" as used herein means a straight- or branched-chain alkyl group having 1 to 6 carbon atoms such as a methyl group, an ethyl group, a n-propyl group, an isopropyl group, a n-butyl group, a tert-butyl group, a sec-butyl group, a n-pentyl group, a n-hexyl group, and the like.

The term "a halogen atom" as used herein means a fluorine atom, a chlorine atom, a bromine atom, or an iodine atom.

A 1-(2-benzimidazolyl)-1,5-diazacyclooctane compound of the formula (I) of the present invention is a novel compound and can be prepared as follows. For example, it can be prepared by a reaction of a 1-(2-benzimidazolyl)-1, 5-diazacyclooctane compound represented by the following formula or an acid addition salt thereof:

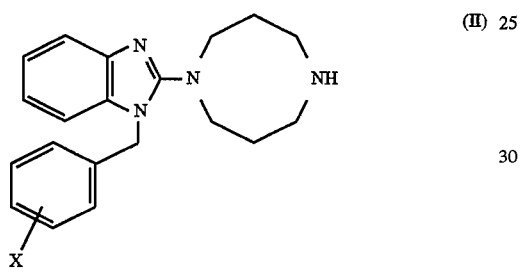

(II)

wherein X has the same meaning as defined above, with a phenylethyl bromide compound represented by the formula:

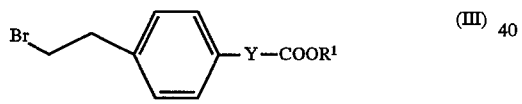

(III)

wherein $R^1$ represents a straight- or branched-chain alkyl group having 1 to 6 carbon atoms; Y has the same meaning as defined above, in the presence of a basic reagent in an inert solvent, and optionally, hydrolyzing the ester product to the corresponding free carboxylic acid.

In the above process, suitable inert solvents include benzene, toluene, tetrahydrofuran, dioxane, acetone, acetonitrile, dimethylsulfoxide, N,N-dimethylformamide, n-butanol, and any other solvent which does not adversely influence this reaction. Suitable basic reagents include potassium carbonate, sodium carbonate, sodium hydrogen carbonate, triethylamine, and the like.

As an alternative to using a basic reagent, an excess amount of the reactant compound represented by the formula (II) may be employed.

In the above process, the reaction of the compound (II) with the compound (III) is known as N-alkylation, and can be conducted at a temperature of about 0° to 150° C.

With respect to invention compounds represented by the formula (I), a compound corresponding to the formula:

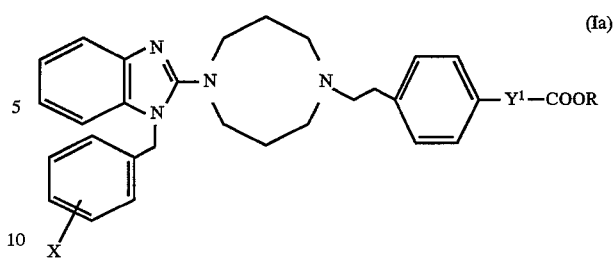

(Ia)

wherein $Y^1$ represents a covalent bond, or a straight- or branched-chain alkylene group having 1 to 6 carbon atoms; X and R have the same meanings as defined above, also can be prepared by a reaction of a 2-halogenobenzimidazole compound represented by the formula:

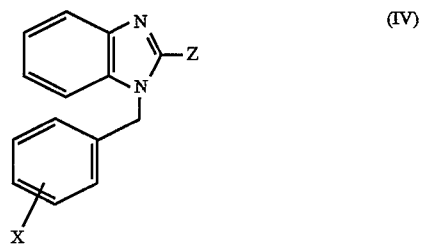

(IV)

wherein z represents a chlorine atom or a bromine atom; X has the same meaning as defined above, with a 1,5-diazacyclooctane compound represented by the formula:

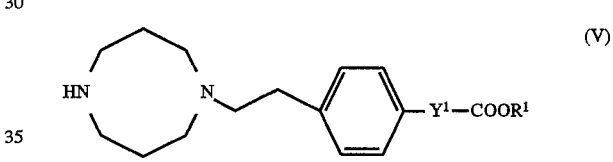

(V)

wherein $R^1$ and $Y^1$ have the same meanings as defined above, in the presence of a basic reagent in the absence or presence of an inert solvent, and optionally, hydrolyzing the ester product to the corresponding free carboxylic acid.

In the above process, suitable inert solvents include benzene, toluene, tetrahydrofuran, dioxane, acetone, acetonitrile, dimethylsulfoxide, N,N-dimethylformamide, n-butanol, and any other solvent which does not adversely influence this reaction. Suitable basic reagents include potassium carbonate, sodium carbonate, sodium hydrogen carbonate, triethylamine, and the like.

As an alternative to using a basic reagent, an excess amount of the reactant compound represented by the formula (V) may be employed.

In the above process, the reaction of the compound (IV) with the compound (V) is known as N-alkylation, and can be conducted at a temperature of about 0° to 150° C.

The compounds represented by the formula (II) used as the starting materials in the process described above are novel, and in one method can be prepared by a reaction of the 2-halogenobenzimidazole compound represented by the formula (IV) with 1,5-diazacyclooctane in the absence or presence of a basic reagent in the absence or presence of an inert solvent.

The 2-halogenobenzimidazole compounds represented by the formula (IV) used as the starting materials in the process described above include known compounds, and can be easily prepared by synthesis methods reported in the chemical literature or analogous methods thereto.

The compounds represented by the formula (V) used as starting materials in the process described above are also novel compounds, and in one method can be prepared by a reaction of the phenylethyl bromide compound represented by the formula (III) with 1,5-diazabicyclo[3,3,0]octane in a nonpolar solvent such as diethyl ether, and then catalytic hydrogenation of the resulting hydrazinium salt compound represented by the formula:

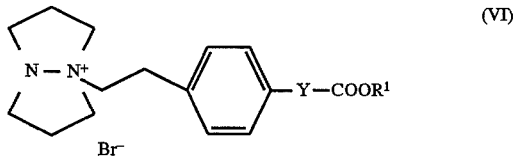

wherein $R^1$ and Y have the same meanings as defined above, in an atmosphere of hydrogen employing a hydrogenating catalyst such as palladium on activated carbon.

The phenylethyl bromide compounds represented by the formula (III) used as the starting materials can be easily prepared by methods described in literature, for example, Journal of the American Chemical Society, Vol. 107, No.5, pp 1429–1430, 1985, or analogous methods thereto.

If there are one or more asymmetric carbon atoms in the substituent Y, the 1-(2-benzimidazolyl)-1,5-diazacyclooctane compounds represented by the formula (I) of the present invention will consist of asymmetric isomers. The configuration of the compounds of the present invention is not limited. The R-isomer, S-isomer or a mixture of R-isomer and S-isomer can be employed in the practice of present invention.

If there are one or more unsaturated bonds in the substituent Y, the 1-(2-benzimidazolyl)-1,5-diazacyclooctane compounds represented by the formula (I) of the present invention will consist of geometrical isomers. All of the geometrical isomers can be employed in the practice of the present invention.

Of the 1-(2-benzimidazolyl)-1,5-diazacyclooctane compounds of the present invention, the compounds wherein X is a fluorine atom are preferred.

Of the 1-(2-benzimidazolyl)-1,5-diazacyclooctane compounds of the present invention, preferred compounds are illustrated by 1-[1-(4-fluorophenylmethyl)-1H-benzimidazol-2yl]-5-[2-(4-isopropoxycarbonylphenyl) ethyl]-1,5-diazacyclooctane, 5-[2-(4-carboxyphenyl)ethyl]-1-[1-(4-fluorophenylmethyl)-1H-benzimidazol-2-yl]-1,5-diazacyclooctane, 5-[2-(4-carboxymethylphenyl)ethyl]-1-[1-(4-fluorophenylmethyl)-1H-benzimidazol-2-yl]-1,5-diazacyclooctane, 1- [1- ( 4- fluorophenylmethyl ) -1H-benzimidazol-2-yl]-5-[2-(4-isopropoxycarbonylmethylphenyl)ethyl]-1,5-diazacyclooctane, 1-[1-(4- fluorophenylmethyl)-1H-benzimidazol-2-yl]-5-[2-[4-(2-methoxycarbonylethyl) phenyl]ethyl]-1,5-diazacyclooctane, 5-[2-[4-(2-ethoxycarbonylethyl)phenyl]ethyl]-1-[1-(4-fluorophenylmethyl)-1H-benzimidazol-2-yl]-1,5-diazacyclooctane, 5-[2-[4-(2-carboxyethyl)phenyl]ethyl]-1-[1-(4-fluorophenylmethyl)-1H-benzimidazol-2-yl]-1,5-diazacyclooctane, 5-[2-[4-(3-ethoxycarbonylpropyl)phenyl] ethyl]-1-[1-(4- fluorophenylmethyl)-1H-benzimidazol-2-yl ]- 1,5-diazacyclooctane, 5-[2-[4-(4-ethoxycarbonylbutyl)phenyl]ethyl]-1-[1-(4-fluorophenylmethyl)-1H-benzimidazol-2 -yl ]-1,5-diazacyclooctane, 5-[2-[4-[(E) -2-ethoxycarbonylvinyl] phenyl]ethyl]-1-[1-(4-fluorophenylmethyl)-1H-benzimidazol-2-yl]-1,5-diazacyclooctane and 5-[2-[4-[(E)-2-carboxyvinyl]phenyl]ethyl]-1-[1-(4- fluorophenylmethyl) -1H-benzimidazol-2-yl]-1,5-diazacyclooctane.

Of the 1-(2-benzimidazolyl)-1,5-diazacyclooctane compounds of the present invention, more preferred compounds are illustrated by 1-[1-(4-fluorophenylmethyl)-1H-benzimidazol-2-yl]-5-[2-[4-(2-methoxycarbonylethyl) phenyl]ethyl]-1,5-diazacyclooctane, 5-[2-[4-(2-ethoxycarbonylethyl)phenyl]ethyl]-1-[1-(4-fluorophenylmethyl)-1H-benzimidazol-2-yl]-1,5-diazacyclooctane, 5-[2-[4-(2-carboxyethyl)phenyl]ethyl]-1-[1-(4-fluorophenylmethyl)-1H-benzimidazol-2-yl ]-1,5-diazacyclooctane, 1-[1-(4-fluorophenylmethyl)-1H-benzimidazol- 2-yl]-5-[2-[4-isopropoxycarbonylphenyl) ethyl]-1,5-diazacyclooctane, 5-[2-(4-carboxyphenyl)ethyl]-1-[1-(4-fluorophenylmethyl)-1H-benzimidazol-2-yl]-1,5-diazacyclooctane, 5-[2-[4-[(E)-2-ethoxycarbonylvinyl] phenyl]ethyl]-1-[1-(4-fluorophenylmethyl)-1H-benzimidazol-2-yl]-1,5-diazacyclooctane and 5-[2-[4-[(E)-2-carboxyvinyl]phenyl]ethyl]-1-[1-(4-fluorophenylmethyl)-1H-benzimidazol-2-yl]-1,5-diazacyclooctane.

Of the 1-(2-benzimidazolyl)-1,5-diazacyclooctane compounds of the present invention, the most preferred compound is 5-[2-[4-(2-carboxyethyl)phenyl]ethyl]-1-[1-(4-fluorophenylmethyl)-1H-benzimidazol-2-yl]-1,5-diazacyclooctane.

The pharmacological activity of the 1-(2-benzimidazolyl)-1,5-diazacyclooctane compounds of the present invention can be confirmed by receptor binding assay in blocking 3H-pyrilamine binding to histamine $H_1$-receptor site in guinea pig cerebellum. The 1-(2-benzimidazolyl)-1,5-diazacyclooctane compounds of the present invention show a potent histamine $H_1$-receptor antagonistic activity, and produce a 50% inhibitory activity in a range of about $10^{-10}$ to $10^{-8}$M (concentration producing 50% reduction of the binding of the labeled ligand). For example, 5-[2-[4-(2-carboxyethyl)phenyl]ethyl]-1-[1-(4-fluorophenylmethyl)-1H-benzimidazol-2-yl]-1,5-diazacyclooctane produced a 50% inhibitory activity at about $5.75 \times 10^{-10}$M.

In the guinea pig antigen-induced bronchoconstriction model, the 1-(2-benzimidazolyl)-1,5-diazacyclooctane compounds of the present invention also show a potent antiallergic activity and a long-lasting efficacy. For example, with 5-[2-[4-(2-carboxyethyl)phenyl]ethyl]-1-[1-(4-fluorophenylmethyl)-1H-benzimidazol-2-yl]-1,5-diazacyclooctane (0.01 mg/ml solution), inhalation for 1 minute (with an ultrasonic nebulizer) inhibited DNP-As (100 µg protein/ml solution, 1 ml/kg, i.v.) -induced bronchoconstriction about 54.6% and about 44.7% at 4 hours and 8 hours after inhalation of this compound, respectively. In comparison, inhalation of Astemizole (0.01 mg/ml solution, inhalation for 1 minute with an ultrasonic nebulizer) inhibited the same DNP-As-induced bronchoconstriction about 37.5% and about 29.3% at 4 hours and 8 hours after the inhalation, respectively.

These findings clearly demonstrated that the compounds of the present invention exhibit potent antihistaminic and antiallergic activities and a long-lasting efficacy by topical administration, and are very useful as therapeutic agents for the treatment of bronchial asthma.

The 1-(2-benzimidazolyl)-1,5-diazacyclooctane compounds of the present invention show a weak cytotoxicity toward normal human epidermal keratinocytes (NHEK) growth. For example, $NR_{50}$ (the concentration of the test compound which causes a 50% reduction in neutral red uptake by a treated cell culture compared with the untreated control culture) value of 5-[2-[4-(2-carboxyethyl)phenyl] ethyl]-1-[1-(4-fluorophenylmethyl)-1H-benzimidazol-2-yl]-1,5-diazacyclooctane is about 789 µM. In comparison, the $NR_{50}$ value of Astemizole is about 4.42 µM.

These findings clearly demonstrated that the 1-(2-benzimidazolyl)-1,5-diazacyclooctane compounds of present invention have a very weak cytotoxicity and a weak topical irritation, and that they are very useful compounds which can be applied to inhalation to the bronchia.

The 1-(2-benzimidazolyl)-1,5-diazacyclooctane compounds represented by the formula (I) of the present invention can be converted into pharmaceutically acceptable salts thereof according to the conventional methods.

The 1-(2-benzimidazolyl)-1,5-diazacyclooctane compounds of the present invention have two basic amino groups, and mono- or di-acids addition salts thereof can be prepared. Examples of such mono- or di-acids addition salts include an inorganic acid addition salt formed with hydrochloric acid, hydrobromic acid, sulfuric acid, nitric acid, phosphoric acid, and the like, and an organic acid addition salt formed with acetic acid, maleic acid, fumaric acid, malic acid, citric acid, oxalic acid, lactic acid, tartaric acid, and the like.

Of the 1-(2-benzimidazolyl)-1,5-diazacyclooctane compounds of the present invention, a compound wherein R represents a hydrogen atom can be converted into sodium salt, potassium salt, calcium salt, and the like.

When a 1-(2-benzimidazolyl)-1,5-diazacyclooctane compound represented by the formula (I) of the present invention or a pharmaceutically acceptable salt thereof is employed for inhalation, a dry mixture of a fine powder of 1-(2-benzimidazolyl)-1,5-diazacyclooctane compound of the present invention and an excipient such as lactose, or a solution or suspension of 1-(2-benzimidazolyl)-1,5-diazacyclooctane compound of the present invention in a suitable diluent such as water or ethyl alcohol, can be administered by inhalation using a suitable inhalator or nebulizer. If desired, a fine powder of 1-(2-benzimidazolyl)-1,5-diazacyclooctane compound of the present invention can be treated with a surface active agent to prevent coaggregation, and a propellant such as air or chlorofluorocarbon can be utilized.

The dosage of 1-(2-benzimidazolyl)-1,5-diazacyclooctane compounds represented by the formula (I) of the present invention may be in the range from about 50 µg to 100 mg per adult human per day depending upon the age, sex, weight of the patient, the type of disease, severity of condition to be treated, and the like.

EXAMPLES

The present invention is further illustrated in more detail by way of the following Reference Examples and Examples.

REFERENCE EXAMPLE 1

1-[1-(4-Fluorophenylmethyl)-1H-benzimidazol-2-yl-1,5-diazacyclooctane

A mixture of 2-bromo-1-(4-fluorophenylmethyl)-1H-benzimidazole (10.07 g) and 1,5-diazacyclooctane (5.60 g) was heated at 80° C. for 1 hour. To the reaction mixture was added distilled water (300 ml), and the mixture was extracted with methylene chloride (300 ml). The extract was washed with water, and dried over anhydrous $MgSO_4$. The solvent was removed under reduced pressure to give 1-[1-(4-fluorophenylmethyl)-1H-benzimidazol-2-yl]-1,5-diazacyclooctane (12.1 g) as a colorless oily liquid.

NMR ($CDCl_3$) δ: 1.75(t, 4H), 2.96(t, 4H), 3.54(t, 4H), 5.23 (s, 2H), 6.97–7.20(m, 7H), 7.58(d, 1H)

REFERENCE EXAMPLE 2

In a similar manner to that described in Reference Example 1, the following compound was prepared by using 2-bromo-1-phenylmethyl-1H-benzimidazole instead of 2-bromo-1-(4-fluorophenylmethyl)-1H-benzimidazole.

1-(1-Phenylmethyl-1H-benzimidazol-2-yl)-1,5

NMR ($CDCl_3$) δ: 1.75(m, 4H), 2.94(m, 4H), 3.55(t, 4H), 5.27 (s, 2H), 6.95–7.10 (m, 2H), 7.15–7.20(m, 3H), 7.25–7.35(m, 3H), 7.58(d, 1H)

REFERENCE EXAMPLE 3

In a similar manner to that described in Reference Example 1, the following compound was prepared by using 2-bromo-1-(4-chlorophenylmethyl)-1H-benzimidazole instead of 2-bromo-1-(4-fluorophenylmethyl)-1H-benzimidazole.

1-[1-(4-Chlorophenylmethyl)-1H-benzimidazol-2-yl]-1,5-diazacyclooctane.

NMR ($CDCl_3$) δ: 1.75(m, 4H), 2.92 (t, 4H), 3.56 (t, 4H), 5.25 (s, 2H), 6.95(d, 1H), 7.05–7.15(m, 3H), 7.20–7.30(m, 3H), 7.59 (d, 1H)

REFERENCE EXAMPLE 4

2-[4-(2-Methoxycarbonylethyl)phenyl]ethyl bromide

A mixture of 4-(2-t-butyldimethylsiloxyethyl) bromobenzene (1.00 g), methyl acrylate (0.55 g), palladium (II) acetate (0.010 g), triphenylphosphine (0.017 g) and N,N,N',N'-tetramethylethylenediamine (0.48 ml) was heated at 140° C. for 24 hours under an atmosphere of argon. To the reaction mixture was added methylene chloride (30 ml), the formed insoluble materials were removed by filtration through a celite column, and the filtrate was concentrated under reduced pressure. To the residue was added diethyl ether (30 ml), and the formed insoluble materials were removed by filtration through a celite column. The filtrate was concentrated to dryness to give methyl 4-(2-t-butyldimethylsiloxyethyl)cinnamate (0.94 g) as a brown oily liquid.

To a solution of methyl 4-(2-t-butyldimethylsiloxyethyl) cinnamate (1.90 g) in ethanol (15 ml) was added a 10% palladium on activated carbon (0.20 g), and the mixture was stirred at room temperature for 4 hours under an atmosphere of hydrogen. The catalyst was removed by filtration through a celite column, and the filtrate was concentrated to dryness under reduced pressure. To the residue was added a 48% hydrobromic acid (15 ml), and the mixture was refluxed for 2 hours. The reaction mixture was poured into an ice-water, and the resulting precipitates were collected by filtration. The obtained crystals were dissolved in an aqueous 2N-NaOH solution, and the solution was washed with diethyl ether. After the aqueous layer was neutralized with a 2N-HCl, the resulting precipitates were collected by filtration, washed with water, and dried at 80° C.

The obtained crystals were dissolved in a methanol (15 ml) solution saturated with HCl, and the solution was refluxed for 2 hours. The solvent was removed under reduced pressure, the residue was quenched with a saturated aqueous $NaHCO_3$ solution, and the mixture was extracted with diethyl ether. The extract was dried over anhydrous $MgSO_4$, and concentrated to dryness under reduced pressure to give 2-[4-(2-methoxycarbonylethyl)phenyl]ethyl bromide (0.80 g) as brown powder.

NMR ($CDCl_3$) δ: 2.62 (t, 2H), 2.92 (t, 2H), 3.12 (t, 2H), 3.53 (t, 2H), 3.66 (s, 3H), 7.14 (m, 4H)

REFERENCE EXAMPLE 5

2-[4-[(E)-2-Ethoxycarbonylvinyl]phenyl]ethyl bromide

In a similar manner to that described in Reference Example 4, ethyl 4-(2-t-butyldimethylsiloxyethyl) cinnamate was prepared by using ethyl acrylate instead of methyl acrylate. To a solution of ethyl 4-(2.t-butyldimethylsiloxyethyl)cinnamate (1.1 g) in tetrahydrofuran (4 ml) was added dropwise tetra-n-butylammonium fluoride (1 mol/l solution in tetrahydrofuran, 3.5 ml), and the mixture was stirred at room temperature for 1.5 hours. The reaction mixture was poured into water, and the mixture was extracted with diethyl ether. The extract was dried over anhydrous $MgSO_4$, and the solvent was removed under reduced pressure. To a solution of the residue and triphenylphosphine (1.07 g) in methylene chloride (10 ml) was added carbon tetrabromide (1.35 g), and the mixture was stirred at room temperature for 30 minutes. The reaction mixture was concentrated under reduced pressure. To the residue was added n-hexane, and the insoluble materials were removed by filtration. The filtrate was concentrated under reduced pressure, and the residue was purified by medium pressure liquid column chromatography on a silica gel column using a mixture of methylene chloride and n-hexane (1:1) as eluent to give 2-[4-[(E)-2-ethoxycarbonylvinyl]phenyl]ethyl bromide (0.77 g) as an colorless oily liquid.

NMR ($CDCl_3$) δ: 1.32(t, 3H), 3.18(t, 2H), 3.56(t, 2H), 4.28 (q, 2H), 6.42(d, 1H, J=16.0 Hz), 7.24(d, 2H), 7.48 (d, 2H), 7.66(d, 1H, J=16.0 Hz)

REFERENCE EXAMPLE 6

2-[4-(3-Ethoxycarbonylpropyl)phenyl]ethyl bromide

To a solution of ethyl 4-(2-t-butyldimethylsiloxyethyl) cinnamate (1.9 g) in tetrahydrofuran (6 ml) was added dropwise tetra-n-butylammonium fluoride (1 mol/l solution in tetrahydrofuran, 6.0 ml), and the mixture was stirred at room temperature for 1.5 hours. To the reaction mixture was added water, and the mixture was extracted with diethyl ether. The extract was dried over anhydrous $MgSO_4$. The solvent was removed under reduced pressure, and the residue was treated according to C. J. Kowalski's method described in J. Am. Chem. Soc., Vol.107, No.5, 1429–1430 (1985) to give 2-[4-(3-ethoxycarbonyl- 1-propenyl)phenyl] ethyl alcohol (0.42 g) as colorless powder.

To a solution of 2-[4-(3-ethoxycarbonyl-1-propenyl) phenyl]ethyl alcohol (0.42 g) in ethanol was added a 10% palladium on activated carbon (0.05 g), and the mixture was stirred at room temperature for 2 hours under an atmosphere of hydrogen. The catalyst was removed by filtration through a celite column, and the filtrate was concentrated under reduced pressure. To a solution of the residue and triphenylphosphine (0.55 g) in methylene chloride (5 ml) was added carbon tetrabromide (0.70 g), and the mixture was stirred at room temperature for 30 minutes. The solvent was removed under reduced pressure, and the residue was purified by medium pressure liquid column chromatography on a silica gel column using a mixture of n-hexane and methylene chloride (3:1) as eluent to give 2-[4-(3-ethoxycarbonylpropyl)phenyl]ethyl bromide (0.31 g) as a colorless oily liquid.

NMR ($CDCl_3$) δ: 1.22(t, 3H), 1.94(m, 2H), 2.30(t, 2H), 2.62 (m, 2H), 3.12(t, 2H),3.53(t, 2H), 4.11(q, 2H), 7.12 (brs, 4H)

REFERENCE EXAMPLE 7

2-[4-(4-Ethoxycarbonylbutyl)phenyl]ethyl bromide

To a solution of 4-(2-t-butyldimethylsiloxyethyl) bromobenzene (4.29 g) in tetrahydrofuran (30 ml) was added n-butyllithium (1.64 mol/l solution in tetrahydrofuran, 9.0 ml) at −78° C., and the mixture was stirred at the same temperature for 15 minutes. To the reaction mixture was added N,N-dimethylformamide (1.3 ml), and the mixture was stirred at room temperature for 30 minutes. The reaction mixture was poured into water, and the mixture was extracted with diethyl ether. The extract was concentrated to dryness under reduced pressure to give 4-(2-t-butyldimethylsiloxyethyl)benzaldehyde(3.59 g)To a solution of ethyl triphenylphosphranylidenebutylate (2.22 g), which was prepared from (3-carboethoxypropyl) triphenylphosphonium bromide and sodium bis (trimethylsilyl)amide, in tetrahydrofuran (25 ml) was added 4-(2-t-butyldimethylsiloxyethyl)benzaldehyde (1.57 g) at −78° C., and the mixture was stirred at the same temperature for 4 hours and allowed to stand at room temperature for 12 hours. The reaction mixture was poured into water, and the mixture was extracted with diethyl ether. The extract was washed with brine, dried over anhydrous $MgSO_4$, and the solvent was removed under reduced pressure. To a solution of the residue in acetonitrile (80 ml) was added a 47% hydrofluoric acid (1 ml), and the mixture was stirred at room temperature for 1 hour. The solvent was concentrated under reduced pressure. The residue was dissolved in chloroform, the solution was washed with a saturated aqueous $NaHCO_3$ solution, and dried over anhydrous $MgSO_4$. The solvent was removed under reduced pressure. The residue was purified by medium pressure liquid column chromatography on a silica gel column using a mixture of methylene chloride, diethyl ether and methanol (1:1:1) as eluent to give 2-[4-(4-ethoxycarbonyl-1-butenyl)phenyl]ethyl alcohol (0.35 g).

To a solution of 2-[4-(4-ethoxycarbonyl-1-butenyl) phenyl]ethyl alcohol (0.33 g) in ethanol (10 ml) was added a 10% palladium on activated carbon (0.030 g), and the mixture was stirred at room temperature for 3 hours under an atmosphere of hydrogen. The catalyst was removed by filtration through a celite column, and the solvent was removed under reduced pressure. To a solution of the residue in methylene chloride (5 ml) were added triphenylphosphine (0.387 g) and carbon tetrabromide (0.489 g), and the mixture was stirred at room temperature for 30 minutes. The reaction mixture was concentrated under reduced pressure. To the residue was added a mixture of diethyl ether and n-hexane (1:1), and the insoluble materials were removed by filtration. The filtrate was concentrated to dryness under reduced pressure to give 2-[4-(4-ethoxycarbonylbutyl)phenyl]ethyl bromide (0.52 g) as an oily liquid.

NMR ($CDCl_3$) δ: 1.25(t, 3H), 1.60–1.70(m, 4H), 2.21(m, 2H), 2.60 (m, 2H), 3.14 (t, 2H), 3.55 (t, 2H), 4.12 (q, 2H), 7.10–7.15 (brs, 4H)

REFERENCE EXAMPLE 8

2-[4-(2-Methoxycarbonyl-2-methylpropyl)phenyl] ethyl bromide

To a solution of methyl 4-(2-t-butyldimethylsiloxyethyl) cinnamate (1.53 g) in ethanol (25 ml) was added a 10% palladium on activated carbon (0.15 g), and the mixture was stirred at room temperature for 2 hours under an atmosphere of hydrogen. The catalyst was removed by filtration, and the filtrate was concentrated under reduced pressure. To a solution of the residue in tetrahydrofuran (35 ml) was added lithium bis(trimethylsilyl)amide (1.0 mol/l solution in tetrahydrofuran, 3.9 ml) at −78° C., and the mixture was stirred at the same temperature for 30 minutes. To the reaction mixture was added a solution of iodomethane (0.533 g) in tetrahydrofuran (2 ml), and the mixture was stirred at room temperature for 1 hour. To the reaction mixture was added water, and the mixture was extracted with diethyl ether. The extract was washed with water, and dried over anhydrous $MgSO_4$. The solvent was removed under reduced pressure, and the residue was purified by medium pressure liquid column chromatography on a silica gel column using a mixture of n-hexane and methylene chloride (3:1) as eluent to give 1-(2-t-butyldimethylsiloxyethyl)-4-(2-methoxycarbonylpropyl) benzene (0.724 g) as a colorless oily liquid.

To a solution of lithium diisopropylamide (0.1 mol/l solution in tetrahydrofuran, 15 ml) was added a solution of 1-(2-t-butyldimethylsiloxyethyl)-4-(2-methoxycarbonylpropyl)benzene (0.62 g) in tetrahydrofuran (2 ml) at −78° C., and the mixture was stirred at the same temperature for 30 minutes. To the reaction mixture was added a solution of iodomethane (0.20 g) in tetrahydrofuran (2 ml), and the mixture was stirred at room temperature for 4 hours. To the reaction mixture was added water, and the mixture was extracted with diethyl ether. The extract was washed with water, and dried over anhydrous $MgSO_4$. The solvent was removed under reduced pressure, and the residue was purified by medium pressure liquid column chromatography on a silica gel column using a mixture of n-hexane and methylene chloride (3:1) as eluent to give 1-(2-t-butyldimethylsiloxyethyl)-4-(2-methoxycarbonyl-2-methylpropyl)benzene (0.49 g) as an oily liquid. To a solution of 1-(2-t-butyldimethylsiloxyethyl)-4-(2-methoxycarbonyl-2-methylpropyl)benzene (0.49 g) in tetrahydrofuran (1.5 ml) was added tetra-n-butylammonium fluoride (1 mol/l solution in tetrahydrofuran, 1.34 ml), and the mixture was stirred at room temperature for 1 hour. To the reaction mixture was added water, and the mixture was extracted with diethyl ether. The extract was washed with water, and dried over anhydrous $MgSO_4$. The solvent was removed under reduced pressure, and the residue was purified by medium pressure liquid column chromatography on a silica gel column using a mixture of methylene chloride and diethyl ether (7:1) as eluent to give 2-[4-(2-methoxycarbonyl-2-methylpropyl)phenyl]ethyl alcohol (0.300 g) as an oily liquid. To a solution of 2-[4-(2-methoxycarbonyl-2-methylpropyl)phenyl]ethyl alcohol (0.300 g) in methylene chloride (3 ml) were added carbon tetrabromide (0.48 g) and triphenylphosphine (0.38 g), and the mixture was stirred at room temperature for 1 hour. The solvent was removed under reduced pressure, and the residue was purified by medium pressure liquid column chromatography on a silica gel column using a mixture of n-hexane and methylene chloride (3:1) as eluent to give 2-[4-(2-methoxycarbonyl-2-methylpropyl)phenyl]ethyl bromide (0.323 g) as an oily liquid.

NMR ($CDCl_3$) δ: 1.18(s, 6H), 2.83(s, 2H), 3.15(t, 2H), 3.55 (t, 2H), 3.67(s, 3H),7.09(m, 4H)

REFERENCE EXAMPLE 9

In a similar manner to that described in Reference Example 8, the following compound was prepared by using ethyl 4-(2-t-butyldimethylsiloxyethyl)cinnamate instead of methyl 4-(2-t-butyldimethylsiloxyethyl)cinnamate.

2-[4-(2-Ethoxycarbonyl-2-methylpropyl)phenyl] ethyl bromide.

NMR ($CDCl_3$) 1.19(s, 6H), 1.22(t, 3H), 2.83(s, 2H), 3.15 (t, 2H), 3.52(t, 2H),4.10(q, 2H), 7.09(m, 4H)

REFERENCE EXAMPLE 10

1-[2-[4-(2-Ethoxycarbonylethyl)phenyl]ethyl]-1,5-diazacyclooctane

To a solution of 2-[4-[(E)-2-ethoxycarbonylvinyl]phenyl] ethyl bromide (2.10 g) in diethyl ether (20 ml) was added 1,5-diazabicyclo[3,3,0]octane (0.89 g), and the mixture was stirred at room temperature for 16 hours. The solvent was removed under reduced pressure. To a solution of the residue in ethanol (30 ml) was added a 10% palladium on activated carbon (0.44 g), and the mixture was stirred at room temperature for 5 hours under an atmosphere of hydrogen. The catalyst was removed by filtration through a celite column, and the filtrate was concentrated under reduced pressure. The residue was quenched with an aqueous 1N-NaOH solution (20 ml), and the mixture was extracted with methylene chloride (30 ml). The extract was dried over anhydrous $MgSO_4$, and concentrated to dryness under reduced pressure to give 1-[2-[4-(2-ethoxycarbonylethyl)phenyl] ethyl]-1,5-diazacyclooctane (2.46 g) as a colorless oily liquid.

NMR ($CDCl_3$) δ: 1.24(t, 3H), 1.63(brs, 4H), 2.57–2.78(m, 10H), 2.85 (brs, 4H), 2.93 (t, 2H), 4.12 (q, 2H), 7.12 (brs, 4H)

REFERENCE EXAMPLE 11

In a similar manner to that described in Reference Example 10, the following compound was prepared by using 2-[4-( 2-methoxycarbonyl-2-methylpropyl)phenyl]ethyl bromide instead of 2-[4-[(E)-2-ethoxycarbonylvinyl] phenyl]ethyl bromide.

1-[2-[4-(2-Methoxycarbonyl-2-methylpropyl) phenyl]ethyl]-1,5-diazacyclooctane.

NMR ($CDCl_3$) δ: 1.17 (s, 6H), 1.65 (m, 4H), 2.60–2.80 (m, 8H), 2.84(s, 2H), 2.90 (m, 4H), 3.66(s, 3H), 7.02 (d, 2H), 7.10(d, 2H)

EXAMPLE 1

1-[1-(4-Fluorophenylmethyl)-1H-benzimidazol-2-yl]-5-[2-[4-(2-methoxycarbonylethyl)phenyl]ethyl]-1,5-diazacyclooctane (compound 1)

To a solution of 1-[1-(4-fluorophenylmethyl)-1H-benzimidazol-2-yl]-1,5-diazacyclooctane (12.1 g) in N,N-dimethylformamide (70 ml) were added 4-(2-methoxycarbonylethyl)phenethyl bromide (9.49 g), sodium carbonate (3.71 g) and potassium iodide (0.58 g), and the mixture was heated at 100° C. for 1 hour. The reaction mixture was poured into an ice-water (200 ml), and the mixture was extracted with methylene chloride (200 ml). The extract was washed with water, and dried over anhydrous $MgSO_4$. The solvent was removed under reduced pressure, and the residue was purified by medium pressure liquid column chromatography on a silica gel column using a mixture of methylene chloride, diethyl ether and methanol (1:1:0.25) as eluent to give 1-[1-(4-fluorophenylmethyl)-1H-benzimidazol-2-yl]-5-[2-[4-(2-methoxycarbonylethyl) phenyl]ethyl]-1,5-diazacyclooctane (11.38 g) as a colorless oily liquid.

NMR ($CDCl_3$) δ: 1.77(t, 4H), 2.58(t, 2H), 2.71(t, 2H), 2.88 (m, 8H), 3.48 (m, 4H), 3.65 (s, 3H), 5.17 (s, 2H), 6.95–7.20 (m, 11H), 7.52 (d, 1H) IR (neat): 1740, 1540, 1510 $cm^{-1}$

EXAMPLE 2

In a similar manner to that described in Example 1, the following compounds were prepared by using corresponding phenethyl bromide derivative instead of 4-(2-methoxycarbonylethyl)phenethyl bromide.

1-[1-(4-Fluorophenylmethyl)-1H-benzimidazol-2-yl]
-5-[2-[4-(2-methoxycarbonyl-2-methylpropyl)
phenyl]ethyl]-1,5-diazacyclooctane (compound 2)

NMR (CDCl$_3$) δ: 1.15(s, 6H), 1.80 (brs, 4H), 2.65–2.95 (m, 10H), 3.50(m, 4H), 3.65(s, 3H), 5.18(s, 2H), 6.92–7.23 (m, 11H), 7.55 (d, 1H) IR (neat): 1740, 1540, 1510 cm$^{-1}$ Mass (FAB) M/Z: 557 (M+H)$^+$ 5-[2-[4-(E)-2-Ethoxycarbonylvinyl]phenyl]ethyl]-1-
[1-(4-fluorophenylmethyl)- 1H-benzimidazol-2-yl]-
1,5-diazacyclooctane (compound 3)

NMR (CDCl$_3$) δ: 1.34 (t, 3H), 1.77 (m, 4H), 2.7 6 (m, 8H), 3.50 (m, 4H), 4.26(q, 2H),5.12(s, 2H), 6.36(d, 1H, J=16.0 Hz), 6.90–7.20 (m, 9H), 7.38 (d, 2H), 7.55 (d, 1H), 7.63 (d, 1H, J=16.0 Hz)

5-[2-[4-(2-Ethoxycarbonyl-2-methylpropyl)phenyl]
ethyl]-1-[1-(4-fluorophenylmethyl)-1H-
benzimidazol-2-yl]-1,5-diazacyclooctane
(compound 4)

NMR (CDCl$_3$) δ: 1.14(s, 6H), 1.24(t, 3H), 1.78(bs, 4H), 2.65–2.85(m, 10H), 3.50(m, 4H), 4.10(q, 2H), 5.18 (d, 2H), 6.92–7.20 (m, 11H), 7.55 (d, 1H)

5-[2-[4-(3-Ethoxycarbonylpropyl)phenyl]ethyl]-1-
[1-(4-fluorophenylmethyl)-1H-benzimidazol-2-yl]-1,
5-diazacyclooctane (compound 5)

NMR (CDCl$_3$) δ: 1.25 (t, 3H), 1.80 (brs, 4H), 1.92 (m, 2H), 2.30 (t, 2H), 2.60(t, 2H), 2.78(brs, 8H), 3.52(m, 4H), 4.12(q, 2H), 5.18(s, 2H), 6.93–7.20 (m, 11H), 7.55 (d, 1H)

5-[2-[4-(4-Ethoxycarbonylbutyl)phenyl]ethyl]-1-[1-
(4-fluorophenylmethyl)- 1H-benzimidazol-2-yl]-1,5-
diazacyclooctane (compound 6)

NMR (CDCl$_3$) δ: 1.25(t, 3H), 1.65(m, 4H), 1.78(brs, 2H), 1.85 (brs, 2H), 2.31 (t, 2H), 2.60 (m, 2H), 2.70–2.90 (m, 8H), 3.51(m, 4H), 5.18(s, 2H), 6.95–7.20 (m, 11H), 7.55 (d, 1H)

1-[1-(1-Fluorophenylmethyl)-1H-benzimidazol-2-
yl]- 5-[2 -(4-isopropoxycarbonylphenyl)ethyl]-1,5-
diazacyclooctane (compound 7)

NMR (CDCl$_3$) δ: 1.38(d, 6H), 1.79(m, 4H), 2.78(m, 4H), 2.83 (bs, 4H), 3.53(m, 4H), 5.18(s, 2H), 5.26 (m, 1H), 6.98–7.28 (m, 9H), 7.57 (d, 1H), 7.96 (d, 2H)

1-[1-(4-Fluorophenylmethyl)-1H-benzimidazol-2-yl]
-5-[2-(4-isopropoxycarbonylmethylphenyl)ethyl]-1,
5-diazacyclooctane (compound 8)

NMR (CDCl$_3$) δ: 1.23 (d, 6H), 1.78(brs, 4H), 2.78(brs, 8H), 3.51(t, 6H), 4.95 (m, 1H), 5.18 (s, 2H), 6.95–7.19 (m, 11H), 7.55 (d, 1H) IR (neat): 1726, 1510 cm$^{-1}$ Mass (FAB) M/Z: 543 (M+H)$^+$

EXAMPLE 3

In a similar manner to that described in Example 1, the following compound was prepared by using 1-[1-(4-chlorophenylmethyl)-1H-benzimidazol-2-yl]-1,5-diazacyclooctane instead of 1-[1-(4-fluorophenylmethyl)-1H-benzimidazol-2-yl]-1,5-diazacyclooctane, and using 2-[4-(2-methoxycarbonyl-2-methylpropyl)phenyl]ethyl bromide instead of 4-(2-methoxycarbonylethyl)phenethyl bromide.

1-[1-(4-Chlorophenylmethyl)-1H-benzimidazol-2-yl]
-5-]2-[4-(2-methoxycarbonyl-2-methylpropyl)
phenyl]ethyl]-1,5-diazacyclooctane (Compound 9).

NMR (CDCl$_3$) δ: 1.15(s, 6H), 1.75(m, 4H), 2.60–2.90(m, 10H), 3.50(m, 4H), 3.65 (s, 3H), 5.18(s, 2H), 6.90–7.40 (m, 11H), 7.55 (d, 1H) IR (neat): 1740, 1540 cm$^{-1}$ Mass (FAB) M/Z: 573 (M+H)$^+$

EXAMPLE 4

5-[2-[4-(2-Carboxyethyl)phenyl]ethyl]-1-[1-(4-
fluorophenylmethyl)-1H-benzimidazol-2-yl]-1,5-
diazacyclooctane sodium salt (Compound 10)

To a solution of 1-[1-(4-fluorophenylmethyl)-1H-benzimidazol-2-yl]-5-[2-[4-(2-methoxycarbonylethyl)phenyl]ethyl]-1,5-diazacyclooctane (6.479) in methanol (100 ml) was added an aqueous 2N-NaOH solution (9.2 ml), and the mixture was heated at 60° C. for 1 hour. The solvent was removed under reduced pressure, and the residue was purified by medium pressure liquid column chromatography on an ODS column using a mixture of methanol and water (65:35) as eluent to give 5-[2-[4-(2-carboxyethyl)phenyl]ethyl]-1-[1-(4-fluorophenylmethyl)-1H-benzimidazol-2-yl]-1,5-diazacyclooctane sodium salt (5.74 g) as white powder.

NMR (CDCl$_3$) δ: 1.62(brs, 4H), 2.42(brs, 2H), 2.58 (brs, 8H), 2.74(brs, 2H), 3.32(brs, 4H), 5.05(brs,2H), 6.70–7.10 (m, 11H), 7.42 (d, 1H) IR (KBr): 1600, 1560, 1540 cm$^1$ Mass (FAB) M/Z: 537 (M+H)$^+$

EXAMPLE 5

In a similar manner to that described in Example 4, the following compounds were prepared by treating the corresponding compound in Example 2 instead of 1-[1-(4-fluorophenylmethyl)-1H-benzimidazol-2-yl]-5-[2-[4 -(2 -methoxycarbonylethyl)phenyl]ethyl]-1,5-diazacyclooctane.

5-[2-(4-Carboxyphenyl)ethyl]-1-[1-(4-
fluorophenylmethyl)-1H-benzimidazol-2-yl]-1,5-
diazacyclooctane sodium salt (compound 11)

NMR (DMSO-d$_6$) δ: 1.83(m, 4H), 2.78(m, 4H), 2.82(m, 4H), 3.58 (m, 4H), 5.43(s, 2H),7.07(m, 1H), 7.14–7.31 (m, 8H), 7.43 (d, 1H), 7.84(d, 2H) IR (KBr): 1550, 1590 cm$^{-1}$ Mass (FAB) M/Z: 509 (M+H)$^+$ 5-[2-(4-Carboxymethylphenyl)ethyl]-1-[1-(4-
fluorophenylmethyl)-1H-benzimidazol-2-yl]-1,5-
diazacyclooctane sodium salt compound 12)

NMR (CDCl$_3$) δ: 1.64(brs, 4H), 2.59 (brs, 8H), 3.24 (brs, 2H), 3.39 (brs, 4H), 5.08(s, 2H), 6.86–7.15(m, 11H), 7.50 (d, 1H) IR (neat): 1545, 1510 cm$^{-1}$ Mass (FAB) M/Z: 523 (M+H) $^+$ 5-[2-[4-(3-Carboxypropyl)phenyl]ethyl]-1-[1-(4-
fluorophenylmethyl)-1H-benzimidazol-2-yl]-1,5-
diazacyclooctane sodium salt (compound 13)

NMR (CDCl$_3$) δ: 1.55–1.85(m, 6H), 2.08 (brs, 2H), 2.39 (brs, 2H), 2.50–2.75 (m, 8H), 3.43(brs, 4H), 5.10(s, 2H), 6.80–7.20(m, 11H), 7.51 (d, 1H) IR (neat): 1600, 1550, 1515 cm$^{-1}$ Mass (FAB) M/Z: 551 (M+H)$^+$ 5-[2-[4-(4-Carboxybutyl)phenyl]ethyl]-1-[1-(4-fluorophenylmethyl)-1H-benzimidazol-2-yl]-1,5-diazacyclooctane sodium salt (compound 14)

NMR (CDCl$_3$) δ: 1.58(brs, 4H), 1.75(brs, 4H), 2.18(brs, 2H), 2.50–2.70(m, 10H), 3.50(brs, 4H), 5.15(brs, 2H), 6.90–7.20 (m, 11H), 7.52 (d, 1H) IR (neat): 1560, 1550, 1510 cm$^{-1}$ Mass (FAB) M/Z: 565 (M+H)$^+$ 5-2-4-[(E)-2-Carboxyvinyl]phenyl]ethyl]-1-[1-(4-fluorophenylmethyl)-1H-benzimidazol-2-yl]-1,5-diazacyclooctane sodium salt (compound 15)

NMR (CDCl$_3$) δ: 1.65(brs, 4H), 2.42–2.70(m, 8H), 3.40 (brs, 4H), 5.03(brs, 2H),6.31(m, 1H), 6.60–7.20 (m, 11H), 7.33(m, 1H), 7.46(brs, 1H) IR (KBr): 1640, 1605, 1545, 1515 cm$^{-1}$ Mass (FAB) M/Z: 535 (M+H)$^+$

EXAMPLE 6

5-[2-[4-(2-Carboxyethyl)phenyl]ethyl]-1-[1-(4-fluorophenylmethyl)-1H-benzimidazol-2-yl]-1,5-diazacyclooctane (compound 16)

A pH of a solution of 5- [2- [4- (2-carboxyethyl)phenyl]ethyl]-1-[1-(4-fluorophenylmethyl)-1H-benzimidazol-2-yl]-1,5-diazacyclooctane sodium salt (5.15 g) in distilled water (100 ml) was adjusted to pH 7 with a 2N-HCl. The resulting white precipitates were collected by filtration, washed with distilled water, and air-dried to give 5- [2- [4-(2-carboxyethyl)phenyl]ethyl]-1-[1-(4-fluorophenylmethyl)-1H-benzimidazol-2-yl]-1,5-diazacyclooctane (4.30 g) as white crystals.

NMR (CDCl$_3$) δ: 1.65(m, 4H), 2.66(m, 8H), 2.82(t, 2H), 2.95 (t, 2H), 3.11 (m, 4H), 5.12 (s, 2H), 6.95–7.20 (m, 11H), 7.52(d, 1H) IR (KBr): 1610, 1540, 1515 cm$^{-1}$ Melting Point: 76°–78° C. Mass (FAB) M/Z: 515 (M+H)$^+$

EXAMPLE 7

In a similar manner to that described in Example 6, the following compound was prepared by treating 5-[2-[4-(2-carboxy-2-methylpropyl)phenyl]ethyl]-1-[1-(4-fluorophenylmethyl)-1H-benzimidazol-2-yl]-1,5-diazacyclooctane sodium salt which was prepared from 1-[1-(4-fluorophenylmethyl)-1H-benzimidazol-2-yl]-5-[2-[4-(2-methoxycarbonyl-2-methylpropyl)phenyl]ethyl]-1,5-diazacyclooctane or 5-[2-[4-(2-ethoxycarbonyl-2-methylpropyl)phenyl]ethyl]-1-[1-(4-fluorophenylmethyl)-1H-benzimidazol-2-yl]-1,5-diazacyclooctane in Example 2 in a similar manner to that described in Example 4, instead of 5-[2-[4-(2-carboxyethyl)phenyl]ethyl]-1-[1-(4-fluorophenylmethyl)-1H-benzimidazol-2-yl]-1,5-diazacyclooctane sodium salt.

5-[2-[4-(2-Carboxy-2-methylpropyl)phenyl]ethyl]-yl-(4-fluorophenylmethyl)-1H-benzimidazol-2-yl]-1,5-diazacyclooctane (Compound 17)

NMR (CDCl$_3$) δ: 1.04 (brs, 6H), 1.66 (brs, 4H), 2.55–2.80 (m, 10H), 3.34(brs, 4H), 5.10(s, 2H), 6.90–7.15 (m, 11H), 7.53 (d, 1H) IR (neat): 1610, 1540, 1510 cm$^{-1}$ Mass (FAB) M/Z: 543 (M+H)$^+$

EXAMPLE 8

1-[1-(4-Fluorophenylmethyl)-1H-benzimidazol-2-yl]-5-[2-[4-2-isopropoxycarbonylethyl)phenyl]ethyl]-1,5-diazacyclooctane (compound 18)

A solution of 5-[2-[4-(2-carboxyethyl)phenyl]ethyl]-1-[1(4-fluorophenylmethyl)-1H-benzimidazol-2-yl]-1,5-diazacyclooctane sodium salt (163 mg) in an isopropanol solution saturated with HCl was refluxed for 4 hours. The solvent was removed under reduced pressure, and the residue was dissolved in methylene chloride (20 ml). The solution was washed with a saturated aqueous NaHCO$_3$ solution and brine. The organic layer was dried over anhydrous MgSO$_4$. The solvent was removed under reduced pressure, and the residue was purified by medium pressure liquid column chromatography on a silica gel column using a mixture of methylene chloride, diethyl ether and methanol (1:1:0.25) as eluent to give 1-[1-(4-fluorophenylmethyl)-1H-benzimidazol-2-yl]-5-[2-[4-(2-isopropoxycarbonylethyl)phenyl]ethyl]-1,5-diazacyclooctane (123mg) as a colorless oily liquid.

NMR (CDCl$_3$) δ: 1.20(d, 6H), 1.77 (m, 4H), 2.55(t, 2H), 2.73 (m, 8H), 2.89(t, 2H), 3.53 (m, 4H), 4.95 (m, 1H), 5.18 (s, 2H), 6.95–7.20 (m, 11H), 7.56 (d, 1H) IR (neat): 1730, 1540, 1510, 1480 cm$^{-1}$

EXAMPLE 9

In a similar manner to that described in Example 8, the following compounds were prepared by treating the corresponding sodium salt compound in Example 4 and 5 instead of 5-[2-[4-(2-carboxyethyl)phenyl]ethyl]-1-[1-(4-fluorophenylmethyl)-1H-benzimidazol-2-yl]-1,5-diazacyclooctane sodium salt.

1-[1-(4-Fluorophenylethyl)-1H-benzimidazol-2-yl-5-[2-[4-(3-isopropoxycarbonylpropyl)phenyl]ethyl]-1,5-diazacyclooctane (compound 19)

NMR (CDCl$_3$) δ: 1.23(d, 6H), 1.79 (brs, 4H), 1.91 (m, 2H), 2.28(t, 2H), 2.60 (t, 2H), 2.78 (brs, 8H), 3.52 (m, 4H), 5.00 (m, 1H), 5.17 ( s, 2H), 6.90–7.20(m, 11H), 7.55 (d, 1H) IR (neat): 1730, 1540, 1520 cm$^{-1}$ 1-[1-(4-Fluorophenylmethyl)-1H-benzimidazol-2-yl]-5-[2-[4-(4-isopropoxycarbonylbutyl)phenyl]ethyl]-1,5-diazacyclooctane (compound 20)

NMR (CDCl$_3$) δ: 1.21(d, 6H), 1.62(m, 4H), 1.78 (brs, 4H), 2.28 (t, 2H), 2.58(t, 2H), 2.70–2.80 (m, 8H), 3.55 (m, 4H), 4.99(m, 1H), 5.18(s, 2H), 6.95–7.20 (m, 11H), 7.55(d, 1H) IR (neat): 1730, 1540, 1515 cm$^{-1}$ 1-[1-(4-Fluorophenylmethyl)-1H-benzimidazol-2-yl]-5-[2-[4-[(E)-2-isopropoxycarbonylvinyl)phenyl]ethyl]-1,5-diazacyclooctane (compound 21)

NMR (CDCl$_3$) δ: 1.31(d, 6H), 1.77(m, 4H), 2.75(m, 8H), 3.50 (m, 4H), 5.07–5.21 (m, 3H), 6.34 (d, 1H, J=16.0 Hz), 6.90–7.20(m, 9H), 7.39(d, 2H), 7.55 (d, 1H), 7.60 (d, 1H, J=16.0 Hz) IR (neat): 1710, 1640, 1610, 1545, 1515 cm$^{-1}$ Mass (FAB) M/Z: 555 (M+H)$^+$ 5-[2-[4-(2-n-Butoxycarbonylethyl)phenyl]ethyl]-1-
[1-(4-fluorophenylmethyl)-1H-benzimidazol-2-yl]-1,
5-diazacyclooctane (compound 22)

NMR (CDCl$_3$) δ: 0.92(t, 3H), 1.35(m, 2H), 1.58(m, 2H), 1.78 (brs, 4H), 2.60(t, 2H), 2.75(m, 8H), 2.90 (t, 2H), 3.51(m, 4H), 4.07(t, 2H), 5.17 (s, 2), 6.93–7.20(m, 11H), 7.56(d, 1H)

EXAMPLE 10

5-[2-[4-(2-Carboxyethyl)phenyl]ethyl]-1-[1-(4-fluorophenylmethyl)-1H-benzimidazol-2-yl]-1,5-diazacyclooctane sodium salt (compound 23)

To a solution of 2-bromo-1-(4-fluorophenylmethyl)-1H-benzimidazole (0.244 g) in n-butanol (1 ml) was added 1-[2-[4-(2-ethoxycarbonylethyl)phenyl]ethyl]-1,5-diazacyclooctane (1.00 g), and the mixture was refluxed for 2 hours. To the reaction mixture was added a saturated aqueous NaHCO$_3$ solution (50 ml), and the mixture was extracted with methylene chloride (30 ml). The extract was washed with water, and dried over anhydrous MgSO$_4$. The solvent was removed under reduced pressure, and the residue was purified by medium pressure liquid column chromatography on a silica gel column using a mixture of methylene chloride, diethyl ether and methanol (1:1:0.25) as eluent to give a mixture (0.369 g) of 5-[2-[4-(2-ethoxycarbonylethyl)phenyl]ethyl]-1-[1-(4-fluorophenylmethyl)-1H-benzimidazol-2-yl]-1,5-diazacyclooctane and 5-[2-[4-(2-n-butoxycarbonylethyl)phenyl]ethyl]-1-[1-(4-fluorophenylmethyl)-1H-benzimidazol-2-yl]-1,5-diazacyclooctane.

To a solution of the mixture (0.369 g) of 5-[2-[4-(2-ethoxycarbonylethyl)phenyl]ethyl]-1-[1-(4-fluorophenylmethyl)-1H-benzimidazol-2-yl]-1,5-diazacyclooctane and 5-[2-[4-(2-n-butoxycarbonylethyl)phenyl]ethyl]-1-[1-(4-fluorophenylmethyl)-1H-benzimidazol-2-yl]-1,5-diazacyclooctane in methanol (3 ml) was added an aqueous 1N-NaOH solution (0.62 ml), and the mixture was stirred at 60° C. for 1 hour. The solvent was removed under reduced pressure, and the residue was purified by medium pressure liquid column chromatography on an ODS column using a mixture of methanol and water (65:35) as eluent to give 5-[2-[4-(2-carboxyethyl)phenyl]ethyl]-1-[1-(4-fluorophenylmethyl)-1H-benzimidazol-2-yl]-1,5-diazacyclooctane sodium salt (0.117 g) as white powder.

Physical and spectral characteristics of the obtained compound above were identical with that of compound 10.

EXAMPLE 11

1-[1-]4-Chlorophenylmethyl)-1H-benzimidazol-2-yl]
-5-[2-[4-(2-methoxycarbonyl-2-methylpropyl)
phenyl]ethyl]-1,5-diazacyclooctane (compound 24)

To a solution of 2-bromo-1-(4-chlorophenylmethyl)-1H-benzimidazole (0.029 g) in n-butanol (0.5 ml) was added 1-[2-[4-(2-methoxycarbonyl-2-methylpropyl)phenyl]ethyl]-1,5-diazacyclooctane (0.102 g), and the mixture was refluxed for 3 hours. The reaction mixture was quenched with a saturated aqueous NaHCO$_3$ solution (30 ml), and the mixture was extracted with methylene chloride (20 ml). The extract was washed with water, and dried over anhydrous MgSO$_4$. The solvent was removed under reduced pressure, and the residue was purified by medium pressure liquid column chromatography on a silica gel column using a mixture of methylene chloride, diethyl ether and methanol (1:1:0.2) as eluent to give 1-[1-(4-chlorophenylmethyl)-1H-benzimidazol-2-yl]-5-[2-[4-(2-methoxycarbonyl-2-methylpropyl)phenyl]ethyl]-1,5-diazacyclooctane (0.030 g) as a colorless oily liquid.

Physical and spectral characteristics of the obtained compound above were identical with that of compound 9.

EXAMPLE 12

In a similar manner to that described in Example 11, the following compound was prepared by using 1- [2- [4-(2-ethoxycarbonylethyl)phenyl]ethyl]-1,5-diazacyclooctane instead of 1-[2-[4-(2-methoxycarbonyl-2-methylpropyl)phenyl]ethyl]-1,5-diazacyclooctane.

1-[1-(4-Chlorophenylmethyl)-1H-benzimidazol-2-yl]
-5-[2-[4-(2-ethoxycarbonylethyl)phenyl]ethyl]-1,5-
diazacyclooctane (compound 25)

NMR (CDCl$_3$) δ: 1.23(t, 3H), 1.77(m, 4H), 2.58(t, 2H), 2.74 (m, 8H), 2.89 (t, 2H), 3.50 (m, 4H), 4.12 (q, 2H), 5.16 (s, 2H), 6.94 (d, 1H), 7.00–7.12 (m, 7H), 7.17(t, 1H), 7.30(d, 2H), 7.55(d, 1H)

EXAMPLE 13

In a similar manner to that described in Example 11, the following compound was prepared by using 2-bromo-1-(4-fluorophenylmethyl)-1H-benzimidazole instead of 2-bromo-1-(4-chlorophenylmethyl)-1H-benzimidazole, and using 1-[2-[4-(2-ethoxycarbonylethyl)phenyl]ethyl]-1,5-diazacyclooctane instead of 1-[2-[4-(2-methoxycarbonyl-2-methylpropyl)phenyl]ethyl]-1,5-diazacyclooctane.

5-[2-[4-(2-Ethoxycarbonylethyl)phenyl]ethyl]-1-[1-
(4-fluorophenylmethyl)-1H-benzimidazol-2-yl]-1,5-
diazacyclooctane (Compound 26)

NMR (CDCl$_3$) δ: 1.24(t, 3H), 1.78(brs, 4H), 2.69(t, 2H), 2.74 (m, 8H), 2.90(t, 2H), 3.52(m, 4H), 4.12 (q, 2H), 5.17 (s, 2H), 6.93–7.20 (m, 11H), 7.56 (d, 1H)

EXAMPLE 14

In a similar manner to that described in Example 6, the following compound was prepared by treating 5-[2-[4-(2-carboxyethyl)phenyl]ethyl]-1-[1-(4-chlorophenylmethyl)-1H-benzimidazol-2-yl]-1,5-diazacyclooctane sodium salt which was prepared from 1-[1-(4-chlorophenylmethyl)-1H-benzimidazol-2-yl]-5-[2-[4-(2-ethoxycarbonylethyl)phenyl]ethyl]-1,5-diazacyclooctane in Example 12 in a similar manner to that described in Example 4, instead of 5-[2-[4-(2-carboxyethyl)phenyl]ethyl]-1-[1-(4-fluorophenylmethyl)-1H-benzimidazol-2-yl]-1,5-diazacyclooctane sodium salt.

5-[2-[4-(2-Carboxyethyl)phenyl]ethyl]-1-[1-(4-
chlorophenylmethyl)-1H-benzimidazol-2-yl]-1,5-
diazacyclooctane (Compound 27)

NMR (CDCl$_3$) δ: 1.62 (brs, 4H), 2.30–2.90 (m, 12H), 3.35 (brs, 4H), 5.07(brs, 2H), 6.80–7.14(m, 9H), 7.20 (d, 2H), 7.50 (d, 1H) IR (neat): 1560, 1540 cm$^{-1}$ Mass (FAB) M/Z: 531 (M+H)$^+$

EXAMPLE 15

5-[2-[4-(2-Carboxyethyl)phenyl]ethyl]-1-[1-(4-fluorophenylmethyl)-1H-benzimidazol-2yl]-1,5-diazacyclooctane.1H$_2$SO$_4$ (Compound 28)

To a solution of 5-[2-[4-(2-carboxyethyl)phenyl]ethyl]-1-[1-(4-fluorophenylmethyl)-1H-benzimidazol-2-yl]-1,5-diazacyclooctane (5.50 g) in methanol (35 ml) was added at once a 10% sulfuric acid (10 ml) under ice-cooling. The resulting precipitates were collected by filtration, dried at 60° C. under reduced pressure to give 5-[2-[4-(2-carboxyethyl)phenyl]ethyl]-1-[1-(4-fluorophenylmethyl)-1H-benzimidazol-2-yl]-1,5-diazacyclooctane.1H$_2$SO$_4$ (6.18 g) as white crystals.

NMR ( DMSO-d$_6$) δ: 2.02(brs, 4H), 2.50(t, 2H), 2.80(t, 2H), 2.95 (m, 2H), 3.34(m, 2H), 3.42(m, 4H), 3.52 (m, 4H), 5.35(s, 2H), 7.05–7.30(m, 11H), 7.45 (d, 1H) IR (KBr): 1690, 1630, 1510 cm$^{-1}$ Elemental Analysis (for C$_{31}$H$_{35}$N$_4$O$_2$F.H$_2$SO$_4$)

|  | C % | H % | N % |
| --- | --- | --- | --- |
| Calcd. | 60.77 | 6.09 | 9.14 |
| Found | 60.89 | 6.09 | 9.15 |

EXAMPLE 16

5-[2-[4-(2-Carboxyethyl)phenyl]ethyl]-1-[1-(4-fluorophenylmethyl)-1H-benzimidazol-2-yl]-1,5-diazacyclooctane.0.5H$_2$SO$_4$ monohydrate (Compound 29)

To a solution of 5- [2- [4- (2-carboxyethyl)phenyl]ethyl] -1-[1-(4- fluorophenylmethyl)-1H-benzimidazol-2-yl]-1,5-diazacyclooctane (0.5 g) in methanol (15 ml) and water (5 ml) was added slowly a 10% sulfuric acid (4.9 ml). The resulting precipitates were collected by filtration, and dried under reduced pressure at 50° C. to give 5-[2-[4-(2-carboxyethyl)phenyl]ethyl]-1-[1-(4-fluorophenylmethyl)-1H-benzimidazol-2-yl]-1,5-diazacyclooctane.0.5H$_2$SO$_4$ monohydrate (4.36 g) as white crystals.

NMR (DMSO-d$_6$) δ: 1.92 (brs, 4H), 2.51 (t, 2H), 2.71 (t, 2H), 2.85 (m, 2H), 3.05–3.30 (m, 6H), 3.50 (m, 4H), 5.32 (s, 2H), 7.05(t, 1H), 7.10–7.30(m, 11H), 7.45 (d, 1H) IR (KBr): 1690, 1620, 1515 cm$^{-1}$ Elemental Analysis (for C$_{31}$H$_{35}$N$_4$O$_2$F.0.5H$_2$SO$_4$.H$_2$O)

|  | C % | H % | N % |
| --- | --- | --- | --- |
| Calcd. | 64.01 | 6.58 | 9.63 |
| Found | 64.26 | 6.29 | 9.51 |

We claim:

1. A 1-(2-benzimidazolyl)-1,5-diazacyclooctane compound represented by the formula:

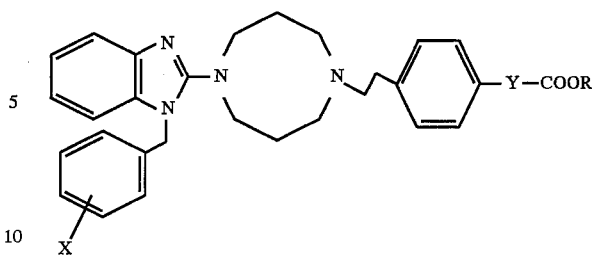

wherein X represents a hydrogen atom or a halogen atom; Y represents a covalent bond, a straight- or branched-chain alkylene group having 1 to 6 carbon atoms, or a straight- or branched-chain alkenylene group having 2 to 6 carbon atoms; R represents a hydrogen atom, or a straight- or branched-chain alkyl group having 1 to 6 carbon atoms; or pharmaceutically acceptable salts thereof.

2. A 1-(2-benzimidazolyl)-1,5-diazacyclooctane compound as claimed in claim 1, represented by the formula:

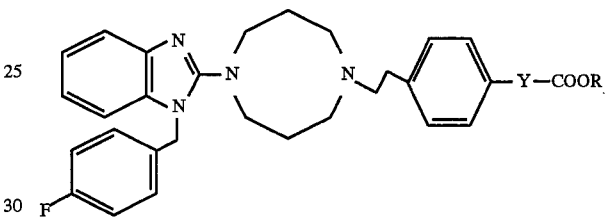

wherein Y represents a covalent bond, a straight- or branched-chain alkylene group having 1 to 6 carbon atoms, or a straight- or branched-chain alkenylene group having 2 to 6 carbon atoms; R represents a hydrogen atom, or a straight- or branched-chain alkyl group having 1 to 6 carbon atoms; or pharmaceutically acceptable salts thereof.

3. The compound, as claimed in claim 2, represented by the formula:

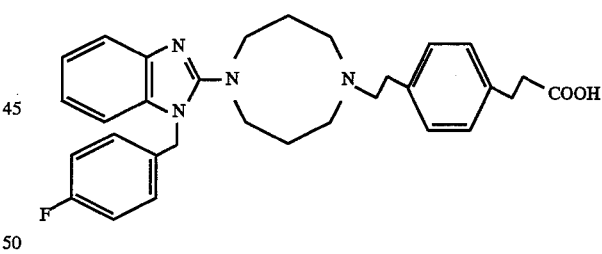

; or pharmaceutically acceptable salts thereof.

4. The compound, as claimed in claim 2, represented by the formula:

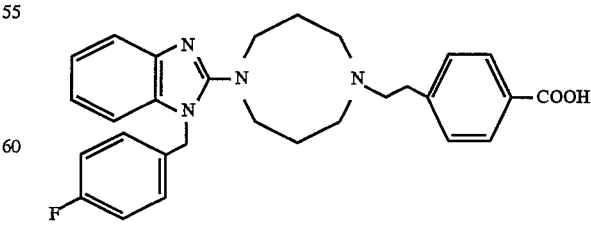

; or pharmaceutically acceptable salts thereof.

5. The compound, as claimed in claim 2, represented by the formula:

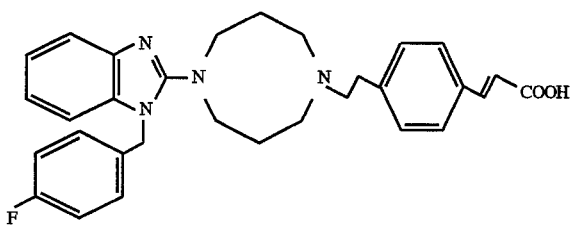

; or pharmaceutically acceptable salts thereof.

6. A pharmaceutical composition for the treatment of bronchial asthma containing, as an active ingredient, a 1-(2-benzimidazolyl)-1,5-diazacyclooctane compound represented by the formula:

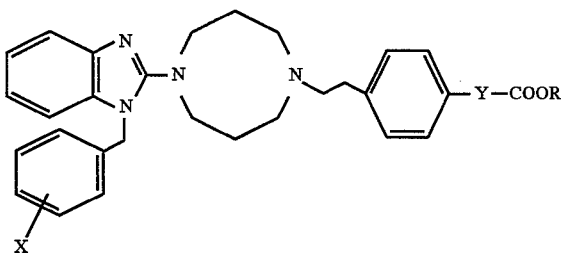

wherein X represents a hydrogen atom or a halogen atom; Y represents a covalent bond, a straight- or branched-chain alkylene group having 1 to 6 carbon atoms, or a straight- or branched-chain alkenylene group having 2 to 6 carbon atoms; R represents a hydrogen atom, or a straight- or branched-chain alkyl group having 1 to 6 carbon atoms; or a pharmaceutically acceptable salt thereof.

7. A pharmaceutical composition as claimed in claim 6, wherein said active ingredient is the compound represented by the formula:

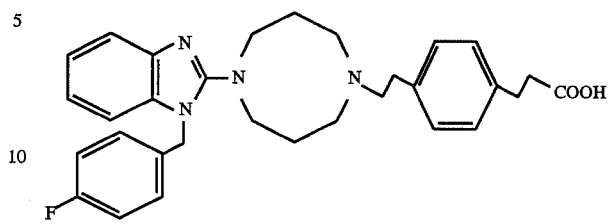

; or a pharmaceutically acceptable salt thereof.

8. A method for the treatment of bronchial asthma, which comprises inhaling to the bronchia a therapeutically effective amount of a 1-(2-benzimidazolyl)-1,5-diazacyclooctane compound or a pharmaceutically acceptable salt thereof of claim 1.

9. The method, as claimed in claim 1, wherein said compound is the compound represented by the formula:

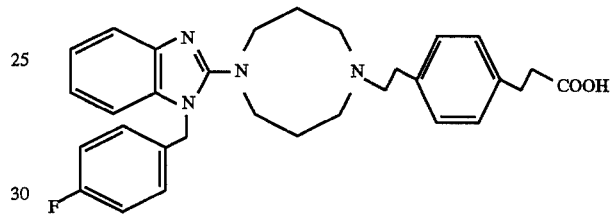

; or a pharmaceutically acceptable salt thereof.

* * * * *

UNITED STATES PATENT AND TRADEMARK OFFICE
CERTIFICATE OF CORRECTION

PATENT NO. : 5,624,948
DATED : Apr. 29, 1997
INVENTOR(S) : Isawa et al

It is certified that error appears in the above-indentified patent and that said Letters Patent is hereby corrected as shown below:

Item [57] Abstract, line 12, "HI-receptor" should be --$H_1$-receptor--.

Col. 1, line 65, delete "methoxycarbonylmethyloxy" and insert --ethoxycarbonylmethyloxy--.

Col. 8, line 1, after "1,5" insert --diazacyclooctane--.

Col. 14, line 23 "(6.479)" should be --(6.47 g)--.

Col. 19, line 25 the "." in the formula should be centered: -- $C_{31}H_{35}N_4O_2F \cdot H_2SO_4$) --.

Col. 19, lines 39 and 50, the "." after "diazacyclooctane" should be centered: -- diazacyclooctane $\cdot 0.5 H_2SO_4$ --.

Col. 19, line 56 the "." should be centered: -- $C_{31}H_{35}N_4O_2F \cdot 0.5H_2SO_4 \cdot H_2O$ --.

Signed and Sealed this

Twelfth Day of August, 1997

Attest:

BRUCE LEHMAN

*Attesting Officer*    *Commissioner of Patents and Trademarks*